(12) United States Patent
Caruba

(10) Patent No.: US 9,186,115 B2
(45) Date of Patent: Nov. 17, 2015

(54) METHOD AND APPARATUS FOR COMPENSATING FOR MAGNETIC FIELD DURING MEDICAL IMAGING

(71) Applicant: Siemens Medical Solutions USA, Inc., Malvern, PA (US)

(72) Inventor: James Frank Caruba, Bartlett, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/314,057

(22) Filed: Jun. 25, 2014

(65) Prior Publication Data

US 2015/0001400 A1 Jan. 1, 2015

Related U.S. Application Data

(60) Provisional application No. 61/841,467, filed on Jul. 1, 2013.

(51) Int. Cl.
| | |
|---|---|
| *G01T 1/20* | (2006.01) |
| *A61B 6/03* | (2006.01) |
| *A61B 6/00* | (2006.01) |
| *G01T 1/16* | (2006.01) |
| *G01T 1/164* | (2006.01) |
| *G01R 33/00* | (2006.01) |
| *G01R 33/025* | (2006.01) |

(52) U.S. Cl.
CPC .............. *A61B 6/037* (2013.01); *A61B 6/5205* (2013.01); *A61B 6/5258* (2013.01); *G01R 33/0076* (2013.01); *G01R 33/0082* (2013.01); *G01R 33/025* (2013.01); *G01T 1/1603* (2013.01); *G01T 1/1647* (2013.01)

(58) Field of Classification Search
CPC ...... A61B 6/037; A61B 6/583; A61B 6/5205; A61B 6/5258; G01T 1/1603; G01T 1/1647; G01R 33/0076; G01R 33/0082; G01R 33/025; G06T 11/005
USPC ........................................................ 250/362
See application file for complete search history.

(56) References Cited

U.S. PATENT DOCUMENTS

| | | | |
|---|---|---|---|
| 4,523,091 A | * | 6/1985 | Persyk .................... 250/214 VT |
| 7,414,248 B1 | | 8/2008 | Kasper et al. |
| 7,449,680 B2 | | 11/2008 | Wang et al. |
| 8,387,183 B2 | | 3/2013 | Caruba |

(Continued)

OTHER PUBLICATIONS

Author: S. Cheenu Kappadath et al, Title: A novel method to evaluate gamma camera rotational uniformity and sensitivity variation, Date: May 5, 2009, Publisher: Am. Assoc. Phys. Med.*

(Continued)

*Primary Examiner* — David J Makiya
*Assistant Examiner* — Taeho Jo
(74) *Attorney, Agent, or Firm* — Peter Kendall

(57) ABSTRACT

A method and apparatus for compensating for the presence of a magnetic field during medical imaging are disclosed. Gamma photons are acquired at a detector. An orientation of the detector (e.g., relative to the surface of the earth) corresponding to the acquisition is determined. Based on the determined detector orientation, one or more compensation value(s) are determined from a memory of a computer, e.g., based on interpolation, parametric computation, or a look-up table. Energy signal variation of a detected signal due to the detector orientation is compensated for by applying the determined compensation value.

24 Claims, 8 Drawing Sheets

(56) References Cited

U.S. PATENT DOCUMENTS

| | | | |
|---|---|---|---|
| 2004/0054248 A1* | 3/2004 | Kimchy et al. | 600/3 |
| 2008/0112603 A1* | 5/2008 | Boyden et al. | 382/131 |
| 2008/0319312 A1* | 12/2008 | Eichler et al. | 600/424 |
| 2011/0251478 A1* | 10/2011 | Wieczorek | 600/411 |
| 2012/0165656 A1* | 6/2012 | Montag et al. | 600/424 |
| 2015/0002150 A1* | 1/2015 | Weissler et al. | 324/309 |

OTHER PUBLICATIONS

Sayed, M. Gary, "Quality Control in Nuclear Medicine II. Planar and Single Photon Emission Computed Tomographic Gamma Camera Apparatus", Turkish Journal of Nuclear Medicine 6(3): 185-189 (1997).

* cited by examiner

METHOD AND APPARATUS FOR COMPENSATING FOR MAGNETIC FIELD DURING MEDICAL IMAGING

CROSS-REFERENCE TO RELATED APPLICATION

This application claims priority under 35 U.S.C. §119(e) from U.S. Provisional Application Ser. No. 61/841,467 filed Jul. 1, 2013, the entirety of which is hereby incorporated by reference herein.

FIELD

Aspects of the present disclosure relate in general to imaging based acquiring gamma photons, and more particularly to calibration and correction techniques for Single Photon Emission Computed Tomography (SPECT) imaging to compensate for the presence of a magnetic field such as the earth's magnetic field.

BACKGROUND

Nuclear medical imaging is a useful technique that is applied in a variety of diagnostic contexts and medical specialties. In one type of nuclear medical imaging known as Single Photon Emission Computed Tomography (SPECT), the primary imaging task is to accurately determine and depict the spatial distribution of a radioactive isotope (radioisotope) used as a tracer (radiotracer) in the imaged object. A radiotracer may also be referred to as a radiopharmaceutical, as it is a pharmaceutical labeled with a radioactive isotope. Typically, the radiotracer travels to a target within the patient's body, and an attached radioactive atom emits gamma ray photons as it undergoes nuclear decay.

A gamma camera (also known as an Anger camera or scintillation camera) has one or more detectors located near the patient for detecting emitted gamma rays that have traveled through a portion of the patient's body. For example, FIG. 1 shows a gamma camera 100 having a detector 105 (e.g., a SPECT detector that detects gamma photons) mounted on a gantry 103 that is secured by a stand 104. Gantry 103 carries a motion guide 106, which in turn carries detector 105. Although one detector is shown in FIG. 1, other configurations are possible, e.g., two detectors 105a and 105b mounted to gantry 103 as shown in the perspective view of FIG. 2. By mounting one or more detectors on gantry 103, the detector(s) can be positioned in various orientations (e.g., relative to the surface of the earth) as the gantry is rotated. For example, in the head-on view of FIG. 1, detector 105 is shown positioned directly above the patient 101 lying on a table top 102, and this orientation may correspond to a gantry rotation angle of 0 degrees (other conventions for defining the rotation angle can be used). As gantry 103 rotates, detector 105 moves along a circular path corresponding to respective gantry rotational orientations. The capability for varying the gantry rotational orientation enables the patient 101 to be imaged from various angles.

For SPECT imaging, gamma camera data are acquired from various view angles or projections and reconstructed in various planes in accordance with the principles of three-dimensional (3D) tomography. A gamma camera used for SPECT is also referred to as a SPECT camera. Gamma cameras for SPECT are described in more detail in Sayed, M., "Quality Control in Nuclear Medicine II. Planar and Single Photon Emission Computed Tomographic Gamma Camera Apparatus," Turkish Journal of Nuclear Medicine 6(3): 185-189 (1997), the entire contents of which are hereby incorporated by reference herein.

Photomultiplier tubes (PMTs) in a gamma camera, which detect and amplify scintillation events, are very sensitive to magnetic fields. One way to address this sensitivity to magnetic fields is to shield individual PMTs with metallic structures. But, such metallic structures that are conventionally used can only extend to the face of a PMT's photocathode, which limits the magnetic shielding effectiveness for the region between the photocathode and one of the electrodes (dynode) of the PMT. Thus, PMTs are susceptible to variation in results due to magnetic fields, despite existing shielding mechanisms.

SUMMARY

In some embodiments of the present disclosure, a method of compensating for the presence of a magnetic field during medical imaging includes acquiring gamma photons at a detector. An orientation of the detector (e.g., relative to the surface of the earth) corresponding to the acquisition is determined. Based on the determined detector orientation, one or more compensation value(s) are determined from a memory of a computer, e.g., based on interpolation, parametric computation, or a look-up table. Energy signal variation of a detected signal due to the detector orientation is compensated for by applying the determined compensation value.

In some embodiments, an apparatus includes a gamma photon detector mounted on a gantry, a memory, one or more computer processors, and a non-transitory computer readable medium. The memory has stored therein a plurality of compensation values corresponding to respective orientations among a plurality of orientations of the detector. The non-transitory computer readable medium has instructions embodied tangibly thereupon, the instructions when executed configured to cause the one or more processors to perform the operations of: determining a first orientation of the detector corresponding to an acquisition of gamma photons by the detector; determining, from the memory, the compensation value corresponding to the first orientation of the detector; and compensating for energy signal variation of a detected signal due to the first rotation of the detector by applying the determined compensation value.

In some embodiments, during a calibration phase, multiple acquisitions of respective pluralities of emitted gamma photons are performed. The multiple acquisitions during the calibration phase (calibration acquisitions) are performed at a detector using a plurality of orientations of the detector relative to the surface of the earth. Data associated with energy values detected by the detector for the respective orientations are stored in a memory. After the calibration phase, another acquisition of another plurality of gamma photons (test acquisition) is performed at the detector. The orientation of the detector relative to the surface of the earth corresponding to the test acquisition is determined. Based on the detector orientation for the test acquisition, a compensation value is determined from a memory of a computer. Energy signal variation of a detected signal due to the detector orientation is compensated for by applying the determined compensation value. After applying the compensation value, an image (e.g., SPECT image) is generated based on data outputted by the detector from the test acquisition.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Various embodiments of the present disclosure provide a way to compensate for effects that a magnetic field may have on detector performance for medical imaging. For example, various embodiments involve applying a compensation factor that is based on a detector orientation or gantry rotational orientation, to compensate for the effects of a spatially varying magnetic field such as the earth's magnetic field, other low level static magnetic fields, or a gravitational field. It is to be understood that for two detectors configured 180 degrees from each other the detector orientation can be related to gantry rotational angle if the detectors are mounted to the gantry, so that ascertaining the orientation of one (detector or gantry) yields the orientation of the other. In general, knowing the detector position (e.g., X, Y) and orientation angle relative to the gantry center of rotation allows the detector orientation to be computed from the gantry rotational angle. The calibration and correction techniques may be used for medical imaging involving detection of gamma photons, e.g., single photon emission computed tomography (SPECT) imaging.

Figure 1:
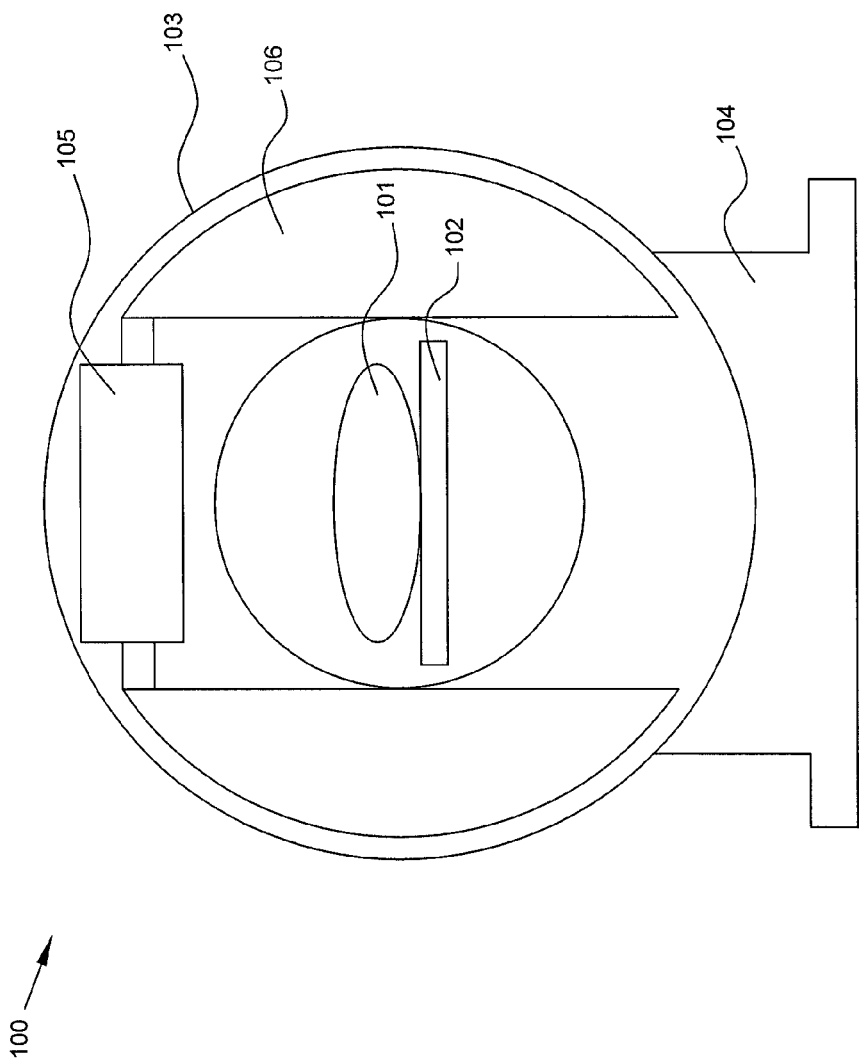
FIG. 1 is an illustration of an example gamma camera.
Figure 2:
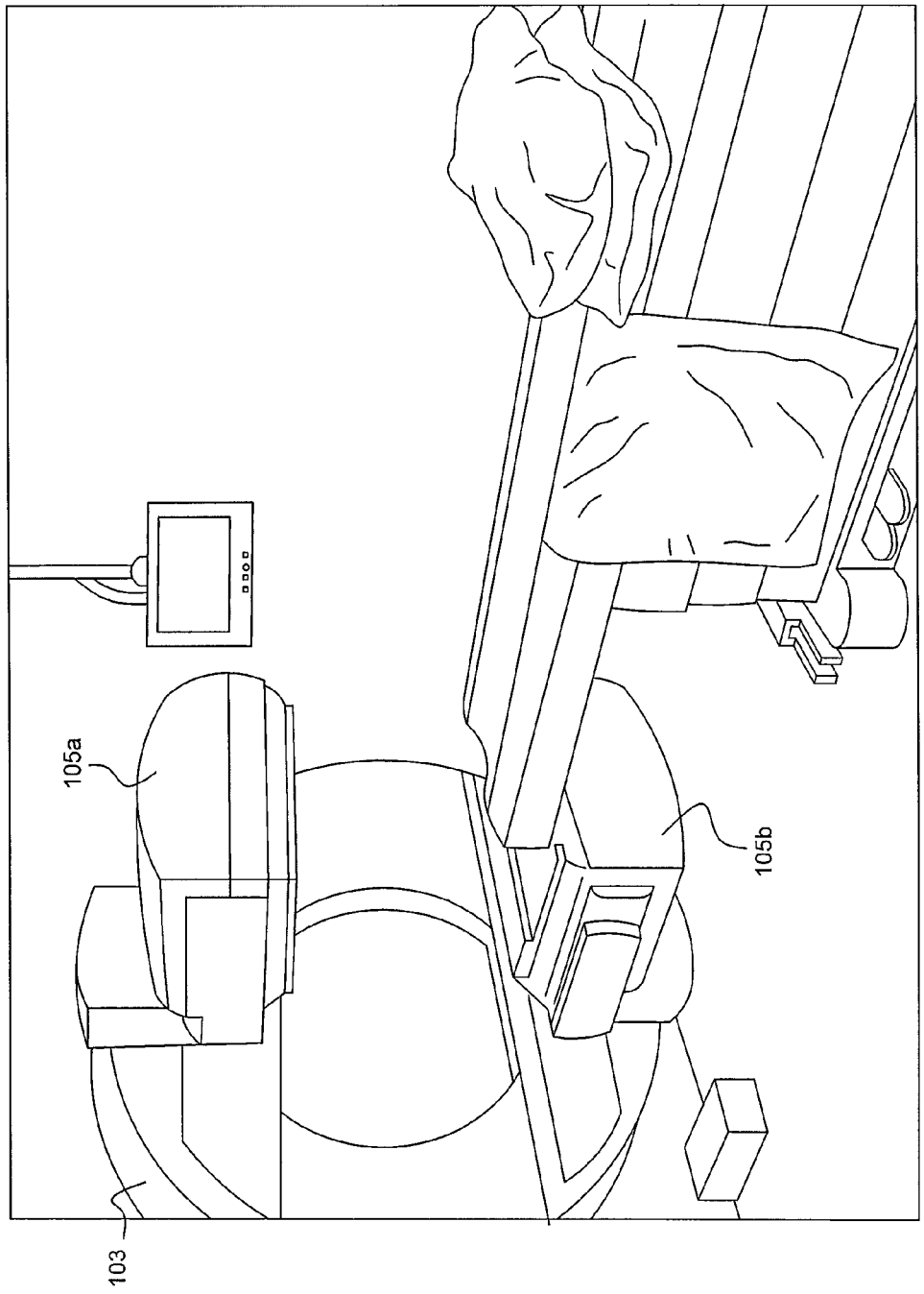
FIG. 2 is a perspective view of an example gamma camera.
Figure 3:
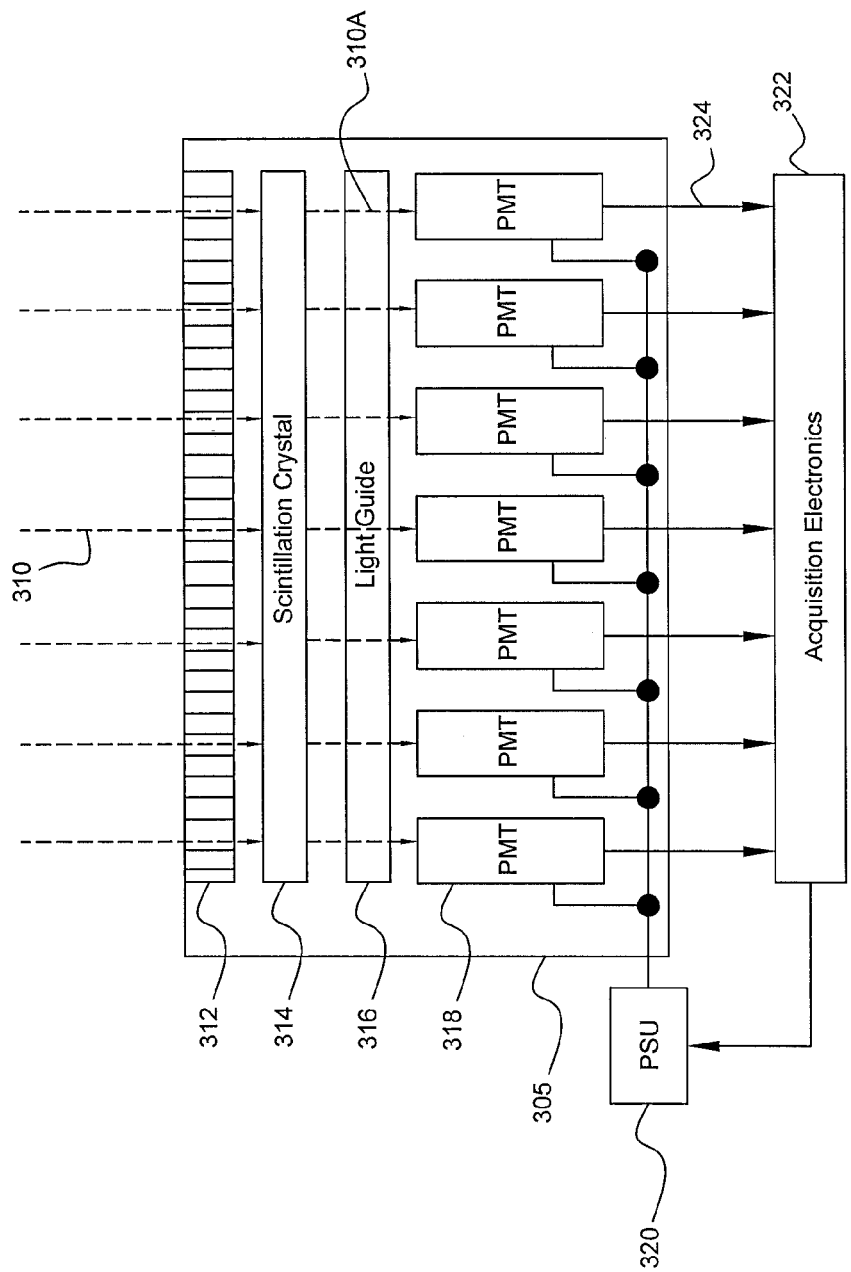
FIG. 3 is a block diagram of a gamma photon detector in accordance with some embodiments.

FIG. 3 is a block diagram of certain components of gamma camera 100, including a detector 305 which may be the same as the detectors of FIGS. 1-2. A parallel hole collimator 312 acts as a guide to channel incident gamma rays 310, emitted by a radiation source (e.g., a radiotracer within a patient's body), to a scintillation crystal 314. The scintillation crystal 314 converts high-energy photons of the gamma rays 310 into visible light comprising lower energy photons. One of ordinary skill in the art understands that power supply unit 320 and/or acquisition electronics system 322 may be considered to be part of the detector.

When a gamma ray 310 strikes and is absorbed in the scintillation crystal 314, the energy of the gamma ray 310 is converted into flashes of light 310A (i.e., a large number of scintillation photons) that emanate and spread from the point at which the gamma ray 310 is absorbed. The scintillation crystal 314 may be formed from any suitable materials known in the art, such as sodium iodide doped with a trace of thallium (NaI(Tl)) or CsI(Tl). The scintillation photons 310A emitted from the scintillation crystal 314 are typically in the visible light region of the electromagnetic spectrum and may have a mean value of about 3 eV for NaI(Tl).

A light guide 316 assists in focusing the scintillation photons 310A from the scintillation crystal 314 to photomultiplier tubes (PMTs) 318. The plurality of PMTs 318 is located adjacent to the light guide 316. In some examples, the number of PMTs may be on the order of about 50 to 100 tubes arranged in a two dimensional array (e.g., a hex-packed array); other numbers of PMTs may be used as well. The basic function of the PMTs 318 is to detect and amplify the scintillation photons 310A (events). Each PMT 318 is operable to detect a fraction of the scintillation photons 110A emanating from the scintillation crystal 314 and produce an analog output signal (e.g., a current) having an amplitude that is proportional to the number of detected scintillation photons 310A. Each PMT 318 includes a light sensitive surface, called the photocathode, which emits electrons in proportion to the number of incident scintillation photons 310A. The emitted electrons, also called photoelectrons, are then electrostatically accelerated into an electron multiplying structure of the PMT 318, which causes an electrical current to be developed at an output of the PMT 318.

The amplitude of the output signal is proportional to the number of photoelectrons generated in the PMT 318 during the time period that scintillation photons 310A are incident. More specifically, the amplitude of the output signal from each PMT 318 is proportional to two basic factors: (i) the number of scintillation photons 310A detected by the PMT 318, and (ii) the gain of the electron multiplying structure of the PMT 318. Thus, after a gamma ray 310 absorption event at the scintillation crystal 314, a given PMT 318 outputs a signal that can be used (with other signals from other PMTs 318) to determine the location of the gamma ray 310 absorption event. Assuming that the analog output signals from the PMTs 318 are current signals, such output signals are subject to a current-to-voltage conversion to yield an analog voltage signal. The analog voltage signals are then digitized using analog to digital ("A/D") converters prior to or as an initial stage in the acquisition electronics system 322. The interconnection circuitry 324 communicates the signals from the PMTs 318 to the acquisition electronics system 322.

The acquisition electronics system 322 is operable to calculate the spatial location and energy level of the incident gamma rays 310 based on the digitized analog output signals from the PMTs 318. From such location information, the acquisition electronics system 322 is then operable to produce X, Y, (position) and E (energy) event data that can be framed into a two dimensional image of the anatomy of the patient 306, which may be displayed on a CRT or other display mechanism. Framing can be accomplished in multiple ways such as (i) through the use of event analyzer windows based on event energy where the analyzer output is framed directly into views for post-acquisition reconstruction or (ii) sending the events X, Y and E together with the detector orientation for storage as list-mode data with post-acquisition framing and reconstruction using the real-time or stored list-mode data directly. The number of scintillation photons producing output in each PMT 318 is inversely related to the distance of the PMT 318 from the point of gamma ray absorption, or event location, within the scintillation crystal 314. Thus, the acquisition electronics system 322 uses this relationship to compute the position (e.g., as an <x, y> pair) of the gamma event from the output signals of a number of the PMTs 318 surrounding the event location.

Figure 4:
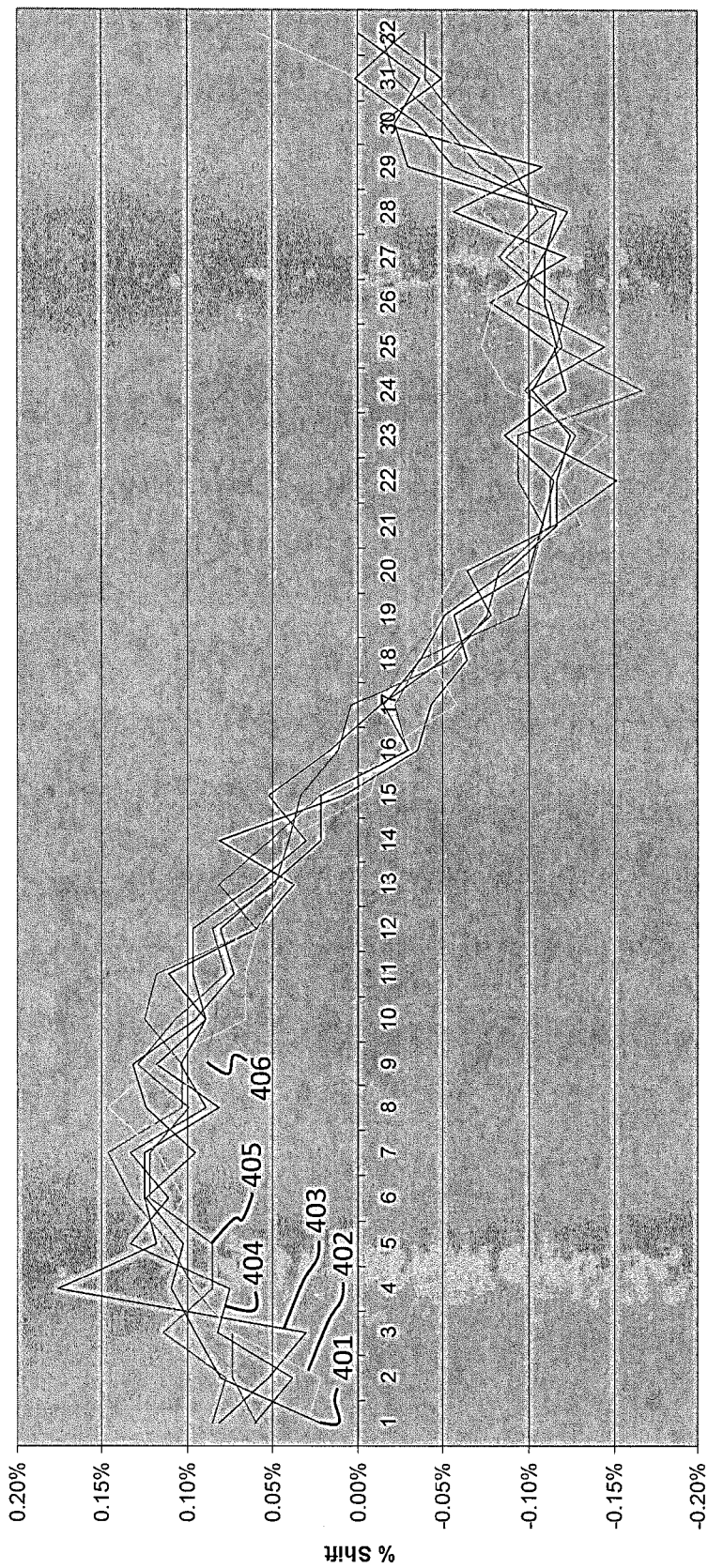
FIG. 4 is a plot of peak energy shift relative to a mean energy level, versus orientation of a detector.

Upon careful study, it has been observed that varying the orientation of the detector (e.g., by rotating the gantry) results in variation of PMT gain due to the earth's magnetic field as the SPECT detector 305 is moved through space. The variation in detector orientation relative to the earth's magnetic field provides a systematic signature, unique to the detector, that can be compensated for in various embodiments. For example, FIG. 4 is a plot that shows an example of energy peak shift (relative to a mean energy level) for detector 305 over various detector orientations, as the gantry 103 (having detector 305 mounted thereto) is rotated through approximately 180 degrees. The x-axis in FIG. 4 corresponds to respective detector orientations, with an acquisition of gamma photons performed at each orientation. The y-axis in FIG. 4 shows deviation (shift) of the detected energy peak relative to a mean energy level computed over all the acquired orientations (i.e., over all 180 degrees of gantry rotation). In FIG. 4, each shift is expressed as a percentage, although it may be expressed in other forms (e.g., 1.001 instead of 0.1%, or an absolute amount of energy instead of an offset). FIG. 4 shows the results for six calibration runs 401, 402, 403, 404, 405, 406 performed at various times during the day, with multiple acquisitions spanning 180 degrees of gantry rotation angle variation performed during each calibration run. As seen in FIG. 4, the variation in peak energy level over orientation is time-invariant, at least at the intraday granularity.

Figure 5:
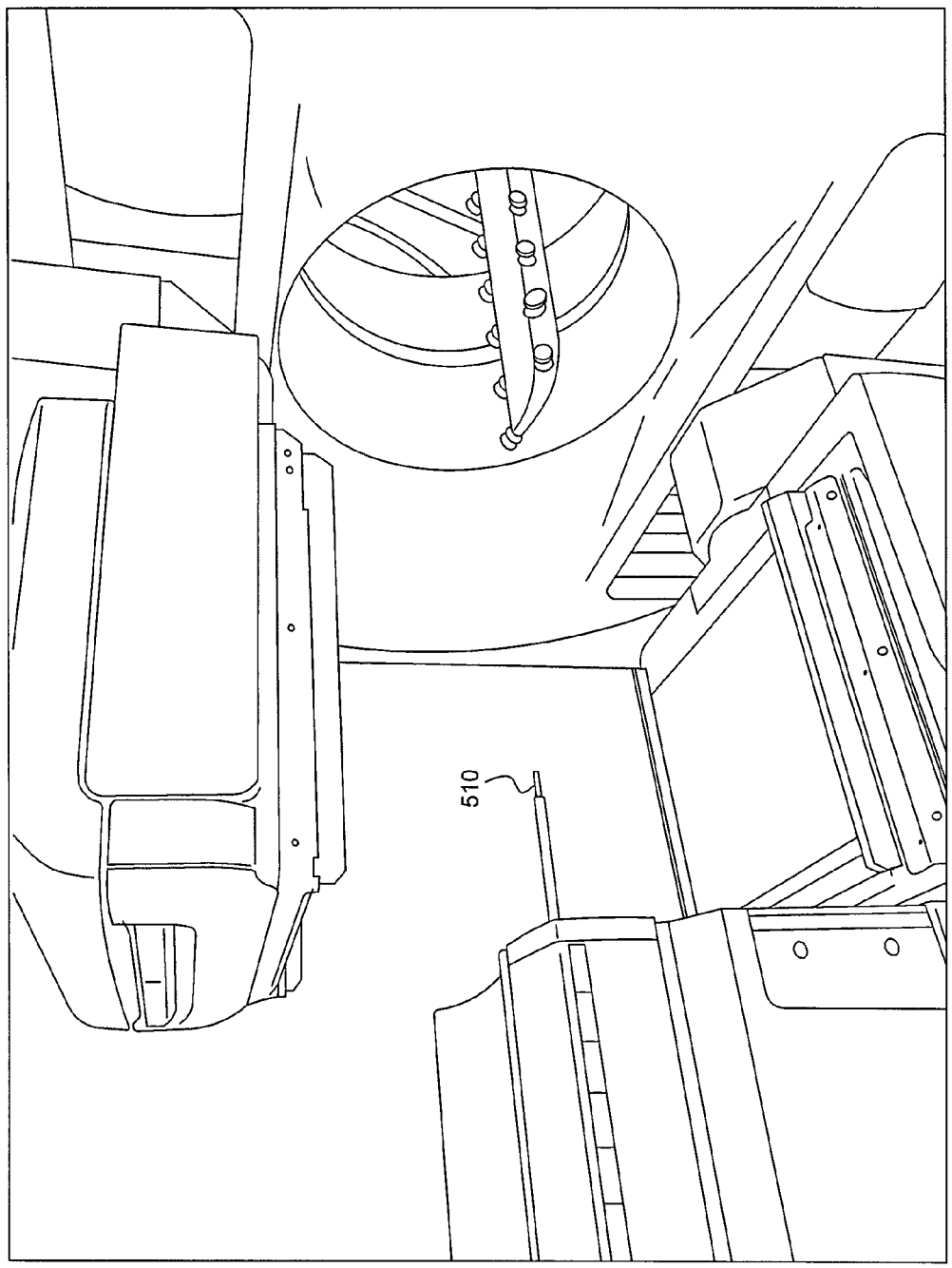
FIG. 5 is an illustration of a radioactive calibration source being imaged during a calibration phase in accordance with some embodiments.

The variation in peak energy level over detector orientation for a given detector can be compensated for by performing a calibration of gamma camera 100 over a range of detector orientations to obtain compensation values. The compensation values can be used for applying corrections to data associated with subsequent gamma photon acquisitions. For example, referring to FIG. 5, a radioactive calibration source 510 (e.g., a point source) can be used for the calibration phase. The orientation of the detector may be varied (e.g., by rotating the gantry to respective rotational settings) to span a predetermined range of rotational variation in a plane of rotation of the detector (e.g., gantry plane) such as 90, 180 or 360 degrees of rotation, or another number of degrees, and an acquisition of gamma photons emitted by point source 510 may be performed at each rotational setting. The peak detected energy for all of the rotational settings may be averaged to yield a mean value. The measured peak energy shift from that mean value may be recorded (e.g., by storing in a memory) for each rotational setting and later retrieved for applying a correction when a patient is imaged using a given detector orientation. Advantageously, such correction can be applied in a data-independent and time-independent manner. While the primary mechanism of the energy peak detector orientation dependency is magnetic, this correction method also compensates for potential secondary mechanisms such as gravity acting on the PMT dynode structures, thereby changing the PMT gain, or on the detector optics, thereby changing the photon collection efficiency.

Figure 6:
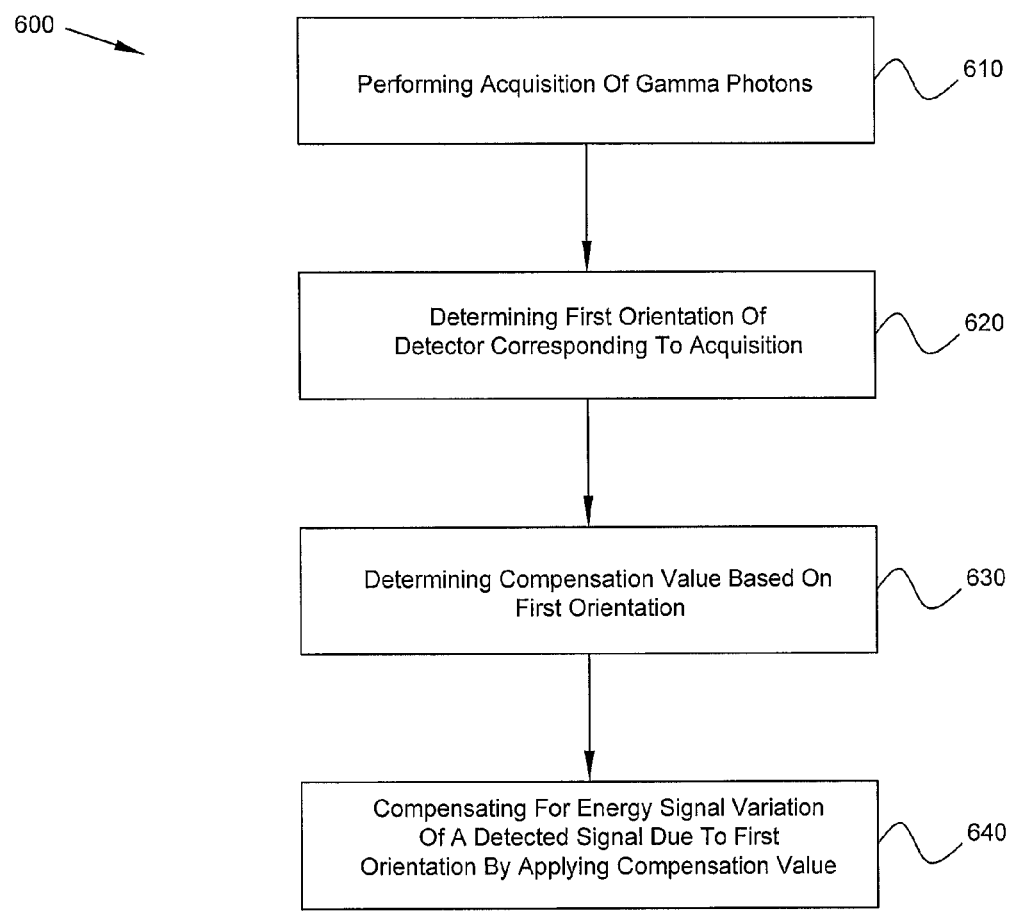
FIG. 6 is a flow diagram of a process in accordance with some embodiments.

FIG. 6 is a flow diagram of a process 600 in accordance with some embodiments. Process 600 is a method of compensating for the presence of a magnetic field during medical imaging. At detector 305, gamma photons are acquired (block 610). An orientation of the detector 305 (e.g., relative to the surface of the earth) corresponding to the acquisition is determined (block 620). An instrument that measures the rotational orientation of the gantry 103 or an instrument that measures the orientation (e.g., 3D orientation) of the detector 305 may be used for this purpose. Based on the determined detector orientation, one or more compensation value(s) are determined (block 630) from a memory of a computer. The compensation value(s) may be determined by direct interpolation, e.g., by interpolating between energy shift data (e.g., as in FIG. 4) retrieved from the memory that correspond to previously calibrated detector orientations. Alternatively, the compensation value(s) may be computed based on parameter(s) retrieved from the memory that specify a best fit curve and that correspond to previously calibrated detector orientations. For example, such parameter(s) may include coefficient(s) of a previously computed best fit polynomial fitted to energy shift data (e.g., as in FIG. 4) corresponding to previously calibrated detector orientations. The parameter(s) may be used to compute the peak energy shift for a given detector orientation, e.g., by evaluating the best fit curve specified by those parameter(s) at a point corresponding to the given detector orientation. Or, the compensation value(s) may be determined from a look-up table containing energy shift data for various detector orientations. Energy signal variation of a detected signal due to the detector orientation is compensated for by applying the determined compensation value(s) (block 640). After applying the compensation value(s), an image (e.g., SPECT image) may be generated.

The compensation value(s) may be applied in various ways to compensate for the effects of the magnetic field. The processing chain for gamma event streams has many stages, and correction may be applied at any stage. For example, the compensation value(s) may be applied directly to the energy value reported by the SPECT detector (i.e., to the overall output of the processing chain). For example, a peak energy shift may be compensated with a multiplication if the format shown in FIG. 4 is used. As one example, the correction or compensation may be represented as $E=Z(1+P(\alpha))$ where E is the corrected energy, Z is the acquired energy, $\alpha$ is an angle defining an orientation of the detector relative to the surface of the earth (the reference geometry may be defined arbitrarily), and P is the percent peak energy shift at angle $\alpha$.

Another option is to leave the event data as reported by the detector and move the energy analyzer window position, e.g., as a function of detector orientation. Moving the window position may correspond to moving the upper or lower bounds of the window, or the center of the window, for example. For example, it is common to place a 15% acceptance energy window centered at the 140 keV Tc99m photopeak. Events falling within the analyzer energy window would be accepted and framed into the respective view while events falling outside the analyzer energy window would be discarded. Moving the 15% energy window position as a function of detector orientation corrects the framed events for detector orientation-based energy variation.

Alternatively, correction can be performed by providing the compensation value(s) as parameter(s) along with the event stream to be corrected during image reconstruction (e.g., in software as opposed to with a voltage correction in hardware). For example, the detector may output data in the form of a vector <x, y, energy> for every event, and that vector may be processed by downstream software. The compensation value(s) can be provided along with the vector.

Yet other options for applying the correction include corrections at the photomultiplier tube (PMT) level. For example, a high voltage adjustment can be applied to one or more PMTs within the detector 305. Such an adjustment may involve varying a voltage between a cathode and an anode of the PMTs, which constitutes a correction applied at the physical layer of the PMTs as a function of detector orientation. Alternatively, a correction may be applied by varying a voltage for one or more dynodes. An individual PMT's integrated event signal may be varied to correct both energy and position.

Thus, corrections can be applied in various ways based on compensation values previously obtained during calibration. The variety of compensation techniques provides flexibility to hardware and software designers of imaging systems.

Figure 7:
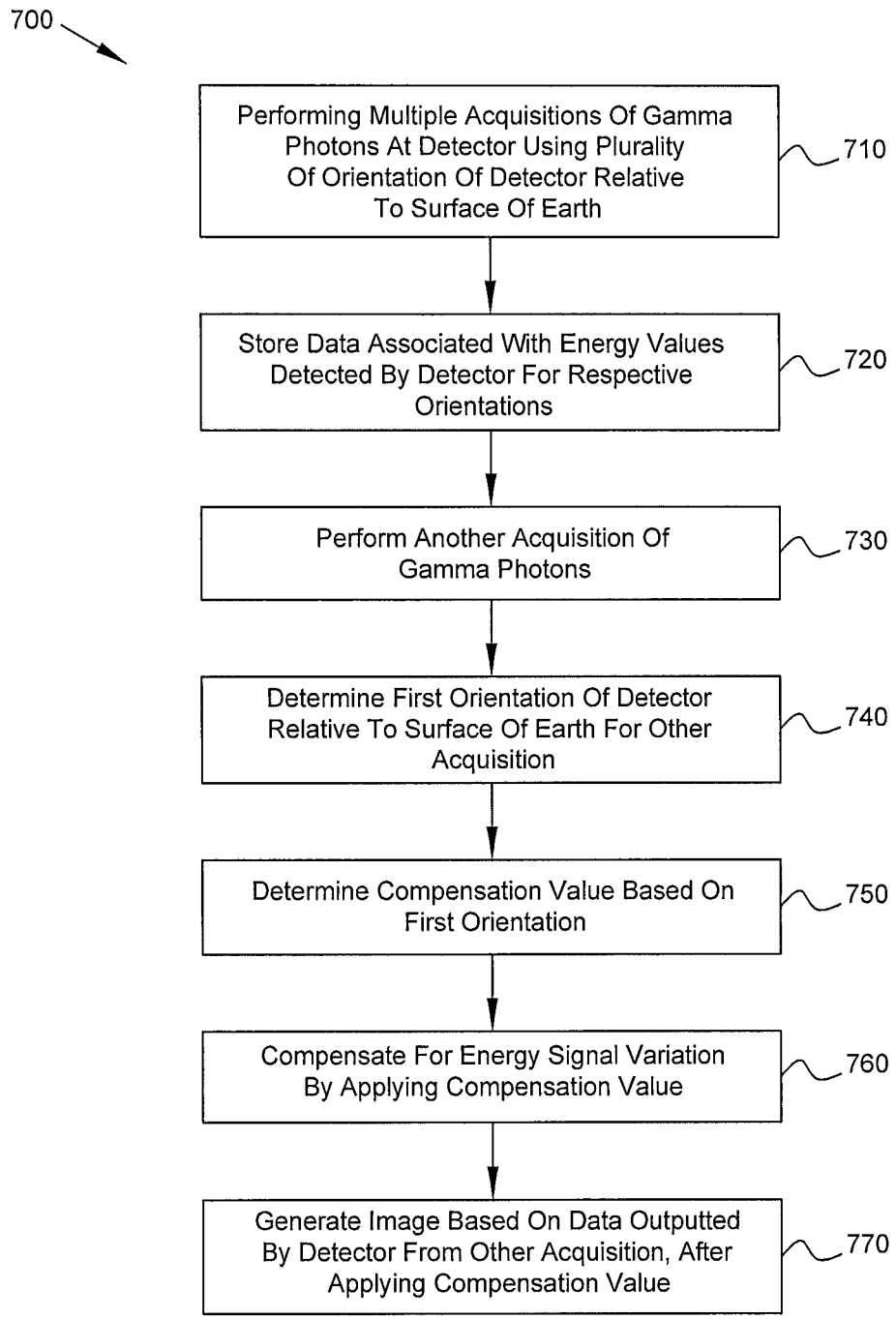
FIG. 7 is a flow diagram of a process in accordance with some embodiments.

FIG. 7 is a flow diagram of a process 700 in accordance with some embodiments. Process 700 is a method of compensating for the presence of a magnetic field during medical imaging. During a calibration phase, multiple acquisitions of respective pluralities of emitted gamma photons are performed (block 710). The multiple acquisitions during the calibration phase (these may be referred to as calibration acquisitions) are performed at detector 305 using a plurality of orientations of the detector relative to the surface of the earth. An instrument that measures the orientation of the detector or an orientation (e.g., rotational angle) of a gantry to which the detector 305 is mounted may be used for this purpose. Data associated with energy values detected by the detector for the respective orientations are stored in a memory (block 720). After the calibration phase, another acquisition of another plurality of gamma photons (this may be referred to as a test acquisition) is performed at detector 305 (block 730). The orientation of detector 305 relative to the surface of the earth corresponding to the test acquisition is determined (block 740). Based on the detector orientation for the test acquisition, a compensation value is determined from a memory of a computer (block 750). Energy signal variation of a detected signal due to the detector orientation is compensated for by applying the determined compensation value (block 760). After applying the compensation value, an image (e.g., SPECT image) is generated based on data outputted by detector 305 from the test acquisition.

In some embodiments, additional calibrations may be performed, on a periodic (e.g., daily, weekly, monthly, or annually) or aperiodic basis after an initial calibration, to ensure quality control. For example, quality control testing may involve sampling a subset of the gantry rotational settings used during the initial calibration, to verify if the measured energy shift data are substantially similar (e.g., within predetermined tolerance) of the initially obtained and recorded data. Using a subset of the overall rotational settings (e.g., three views instead of the 32 views depicted in FIG. 4) is efficient because each acquisition of gamma photons may be relatively time consuming. If an unacceptable set of energy shift data are observed during quality control testing, a new phase of full calibration testing over the entire range of rotational orientations may be instituted.

Figure 8:
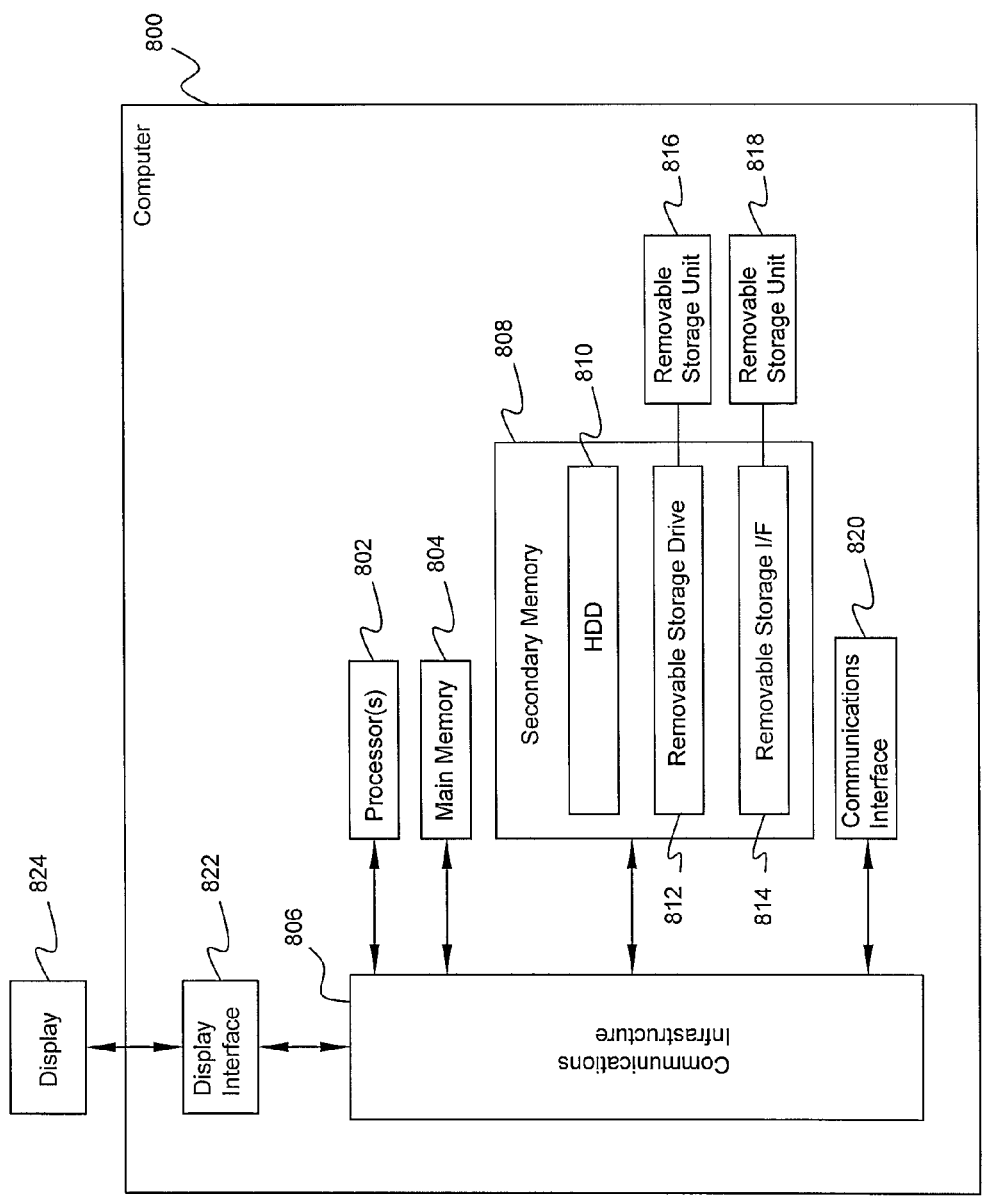
FIG. 8 is an architecture diagram of a computer system that may be used in some embodiments.

FIG. 8 is an architecture diagram of a computer apparatus 800 that may be used in some embodiments. Computer apparatus may be coupled to detector 305 and/or acquisition electronics system 322 and may be used to compute and store the compensation values, retrieve the previously stored compensation values, and/or to apply the compensation values. Computer apparatus 800 may include one or more processors 802. Each processor 802 is connected to a communication infrastructure 806 (e.g., a communications bus, cross-over bar, or network). Computer apparatus 800 may include a display interface 822 that forwards graphics, text, and other data from the communication infrastructure 806 (or from a frame buffer, not shown) for display on the display unit 824.

Computer apparatus 800 may also include a main memory 804, such as a random access memory (RAM), and a secondary memory 808. The secondary memory 808 may include, for example, a hard disk drive (HDD) 810 and/or removable storage drive 812, which may represent a floppy disk drive, a magnetic tape drive, an optical disk drive, a memory stick, or the like as is known in the art. The removable storage drive 812 reads from and/or writes to a removable storage unit 816. Removable storage unit 816 may be a floppy disk, magnetic tape, optical disk, or the like. As will be understood, the removable storage unit 816 may include a computer readable storage medium having tangibly stored therein (embodied thereon) data and/or computer software instructions, e.g., for causing the processor(s) to perform various operations.

In alternative embodiments, secondary memory 808 may include other similar devices for allowing computer programs or other instructions to be loaded into computer apparatus 800. Secondary memory 808 may include a removable storage unit 818 and a corresponding removable storage interface 814, which may be similar to removable storage drive 812, with its own removable storage unit 816. Examples of such removable storage units include, but are not limited to, USB or flash drives, which allow software and data to be transferred from the removable storage unit 816, 818 to computer apparatus 800.

Computer apparatus 800 may also include a communications interface 820. Communications interface 820 allows software and data to be transferred between computer apparatus 800 and external devices. Examples of communications interface 820 may include a modem, Ethernet card, wireless network card, a Personal Computer Memory Card International Association (PCMCIA) slot and card, or the like. Software and data transferred via communications interface 820 may be in the form of signals, which may be electronic, electromagnetic, optical, or the like that are capable of being received by communications interface 820. These signals may be provided to communications interface 820 via a communications path (e.g., channel), which may be implemented using wire, cable, fiber optics, a telephone line, a cellular link, a radio frequency (RF) link and other communication channels.

In this document, the terms "computer program medium" and "non-transitory computer-readable storage medium" refer to media such as, but not limited to, media at removable storage drive 812, or a hard disk installed in hard disk drive 810, or removable storage unit 816. These computer program products provide software to computer apparatus 800. Computer programs (also referred to as computer control logic) may be stored in main memory 804 and/or secondary memory 808. Computer programs may also be received via communications interface 820. Such computer programs, when executed by a processor, enable the computer apparatus 800 to perform the features of the methods discussed herein. For example, main memory 804, secondary memory 808, or removable storage units 816 or 818 may be encoded with computer program code (instructions) for performing operations corresponding to various processes disclosed herein.

It is understood by those familiar with the art that the apparatus described herein may be implemented in hardware, firmware, or software encoded (e.g., as instructions executable by a processor) on a non-transitory computer-readable storage medium.

The apparatuses and processes are not limited to the specific embodiments described herein. In addition, components of each apparatus and each process can be practiced independent and separate from other components and processes described herein.

The previous description of the embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of compensating for the presence of a magnetic field during medical imaging, the method comprising:
 at a detector of a gamma camera, performing an acquisition of gamma photons, wherein the detector is mounted on a gantry;
 determining a first orientation of the detector corresponding to the acquisition;

determining, from a memory of a computer, a compensation value based on the first orientation of the detector; and compensating for energy signal variation of a detected signal due to the first orientation of the detector by applying the compensation value.

2. The method of claim 1, further comprising generating a single photon emission computed tomography (SPECT) image after applying the compensation value.

3. The method of claim 1, further comprising:

performing multiple acquisitions of gamma photons emitted from a calibration source, wherein the multiple acquisitions are performed using a plurality of orientations of the detector; and storing, in the memory, data associated with energy values detected by the detector for the respective orientations.

4. The method of claim 3, wherein the data associated with the energy values include, for each orientation of the detector, an energy peak shift relative to a mean energy value, and the determined compensation value is the energy peak shift corresponding to the first orientation of the detector.

5. The method of claim 3, wherein the plurality of orientations correspond to a range of at least 90 degrees of variation in a plane of rotation of the detector.

6. The method of claim 5, wherein the plurality of orientations correspond to a range of at least 180 degrees of variation in the plane of rotation of the detector.

7. The method of claim 6, wherein the plurality of orientations correspond to a range of at least 360 degrees of variation in the plane of rotation of the detector.

8. The method of claim 1, wherein the memory includes stored therein a plurality of compensation values associated with respective orientations of the detector.

9. The method of claim 1, wherein applying the compensation value includes applying the compensation value to an energy value outputted by the detector.

10. The method of claim 1, wherein applying the compensation value includes varying an energy analyzer window position.

11. The method of claim 1, wherein applying the compensation value includes applying the compensation value during image reconstruction.

12. The method of claim 1, wherein applying the compensation value includes varying a bias voltage for one or more photomultiplier tubes in the gamma camera.

13. The method of claim 12, wherein applying the compensation value includes varying a voltage between a cathode and an anode of the one or more photomultiplier tubes.

14. The method of claim 12, wherein applying the compensation value includes varying a voltage for one or more dynodes of the one or more photomultiplier tubes.

15. The method of claim 1, wherein the compensation value is determined by interpolation.

16. The method of claim 1, wherein the compensation value is computed from one or more parameters specifying a best fit curve.

17. A apparatus comprising:

a gamma photon detector mounted on a gantry;

a memory having stored therein a plurality of compensation values corresponding to respective orientations among a plurality of orientations of the detector;

one or more computer processors; and a non-transitory computer readable medium having instructions embodied tangibly thereupon, the instructions when executed configured to cause the one or more processors to perform the operations of:

determining a first orientation of the detector corresponding to an acquisition of gamma photons by the detector;

determining, from the memory, the compensation value corresponding to the first orientation of the detector; and compensating for energy signal variation of a detected signal due to the first rotation of the detector by applying the determined compensation value.

18. The apparatus of claim 17, wherein the plurality of compensation values stored in the memory include, for each orientation of the detector, an energy peak shift relative to a mean energy value, and wherein determining the compensation value corresponding to the first orientation of the detector includes determining the energy peak shift corresponding to the first orientation of the detector.

19. The apparatus of claim 17, wherein the plurality of orientations correspond to a range of at least 90 degrees of variation in a plane of rotation of the detector.

20. The apparatus of claim 17, wherein applying the determined compensation value includes applying the determined compensation value to an energy value outputted by the detector.

21. The apparatus of claim 17, wherein applying the determined compensation value includes varying an energy analyzer window position.

22. The apparatus of claim 17, wherein applying the determined compensation value includes applying the determined compensation value during image reconstruction.

23. The apparatus of claim 17, wherein applying the determined compensation value includes varying a bias voltage for one or more photomultiplier tubes in the apparatus.

24. A method of compensating for the presence of a magnetic field during medical imaging, the method comprising:

during a calibration phase, performing multiple acquisitions of respective pluralities of emitted gamma photons, wherein the multiple acquisitions are performed at a detector using a plurality of orientations of the detector relative to the surface of the earth;

storing, in a memory, data associated with energy values detected by the detector for the respective orientations;

after the calibration phase, at the detector, performing another acquisition of another plurality of gamma photons;

determining a first orientation of the detector relative to the surface of the earth corresponding to the other acquisition;

determining, from a memory of a computer, a compensation value based on the first orientation;

compensating for energy signal variation of a detected signal due to the first orientation of the detector by applying the compensation value; and after applying the compensation value, generating an image based on data outputted by the detector from the other acquisition.

* * * * *